US012186445B2

(12) United States Patent
Simonovsky

(10) Patent No.: US 12,186,445 B2
(45) Date of Patent: Jan. 7, 2025

(54) HAND WASHING VERIFICATION BY CONTAMINATION SENSOR

(71) Applicant: SOAPY CARE LTD., Ness Ziona (IL)

(72) Inventor: Maxim Simonovsky, Rehovot (IL)

(73) Assignee: SOAPY CARE LTD., Ness Ziona (IL)

( * ) Notice: Subject to any disclaimer, the term of this patent is extended or adjusted under 35 U.S.C. 154(b) by 207 days.

(21) Appl. No.: 18/012,519

(22) PCT Filed: Jun. 22, 2021

(86) PCT No.: PCT/IL2021/050760
§ 371 (c)(1),
(2) Date: Dec. 22, 2022

(87) PCT Pub. No.: WO2021/260693
PCT Pub. Date: Dec. 30, 2021

(65) Prior Publication Data
US 2023/0270904 A1   Aug. 31, 2023

Related U.S. Application Data

(60) Provisional application No. 63/043,272, filed on Jun. 24, 2020.

(51) Int. Cl.
*A61L 2/24*   (2006.01)
*A47K 5/12*   (2006.01)
(Continued)

(52) U.S. Cl.
CPC ............ *A61L 2/24* (2013.01); *A47K 5/1217* (2013.01); *A61L 2/18* (2013.01); *A61L 2/28* (2013.01);
(Continued)

(58) Field of Classification Search
CPC ..... A61L 2/18; A61L 2/24; A61L 2/28; A61L 2202/14; A61L 2202/17; A47K 5/1217;
(Continued)

(56) References Cited

U.S. PATENT DOCUMENTS

2009/0211019 A1* 8/2009 Schluttig ............... E03C 1/126
4/584
2014/0327545 A1   11/2014 Bolling et al.
(Continued)

FOREIGN PATENT DOCUMENTS

WO   2012030216 A1   3/2012
WO   2020044351 A1   3/2020

OTHER PUBLICATIONS

PCT International Search Report for International Application No. PCT/IL2021/050760, mailed Oct. 6, 2021, 2pp.
(Continued)

*Primary Examiner* — Tuan N Nguyen
(74) *Attorney, Agent, or Firm* — The Roy Gross Law Firm, LLC; Roy Gross

(57) ABSTRACT

Methods and systems are provided for verifying hygienic hand cleaning including a wash basin, having a contaminant sensor positioned in proximity to a drain of the wash basin, to measure a level of contamination of rinse fluid leaving the wash basin; and a processor and associated memory having instructions that when executed by the processor implement: receiving a signal from the contaminant sensor indicative of the level of contamination; and responsively, determining the level of contamination and comparing the level of contamination with a contamination threshold to determine a hand washing status.

20 Claims, 4 Drawing Sheets

(51) Int. Cl.
  *A61L 2/18*   (2006.01)
  *A61L 2/28*   (2006.01)
  *E03C 1/05*   (2006.01)
  *G08B 21/18*  (2006.01)

(52) U.S. Cl.
  CPC ........... *E03C 1/057* (2013.01); *A61L 2202/14* (2013.01); *A61L 2202/17* (2013.01); *G08B 21/18* (2013.01)

(58) Field of Classification Search
  CPC ......... G08B 21/18; E03C 1/057; E03C 1/126; E03C 1/184
  USPC .............................. 4/668, 669, 623, 650, 294
  See application file for complete search history.

(56) References Cited

U.S. PATENT DOCUMENTS

| | | | |
|---|---|---|---|
| 2018/0047277 A1 | 2/2018 | Thyroff | |
| 2019/0360184 A1* | 11/2019 | Lawinger | ................ E03C 1/182 |
| 2023/0160188 A1* | 5/2023 | Waggott | ................ E03C 1/126 4/222 |

OTHER PUBLICATIONS

PCT Written Opinion for International Application No. PCT/IL2021/050760, mailed Oct. 6, 2021, 6pp.

\* cited by examiner

HAND WASHING VERIFICATION BY CONTAMINATION SENSOR

CROSS-REFERENCE TO RELATED APPLICATIONS

This application is a National Phase of PCT Patent Application No. PCT/IL2021/050760 having International filing date of Jun. 22, 2021, which claims the benefit of priority of U.S. Provisional Patent Application No. 63/043,272, filed Jun. 24, 2020, the contents of which are all incorporated herein by reference in their entirety.

FIELD OF THE INVENTION

The invention generally relates to methods or apparatus for disinfecting or sterilizing, in particular for cleaning hands.

BACKGROUND

A wide variety of organizations, especially those in health-related fields, such as hospitals, food production factories, pharmaceutical factories, and restaurants, are dependent on their employees abiding by proper standards of hand hygiene. Infections and contaminations in such enterprises can have sever, and at times life-threatening consequences.

Hand washing and sanitizing practices in such environments are often dictated by health authorities. However, it is difficult to confirm that an employee has cleaned his hands according to the required regulations. There is thus a need for improved methods of hand washing verification.

SUMMARY

Embodiments of the present invention provide a system and methods for controlling and monitoring hand washing by an individual. It is a further object of the present invention to provide a system and methods for controlling and monitoring hand cleaning by confirming a sufficient level of purity of the rinse fluid (e.g., water) being used to wash the hands, where rinse fluid contamination is measured at a drain of a wash basin.

There is therefore provided by embodiments of the present invention a hand washing system, including a wash basin, having a contaminant sensor positioned in proximity to a drain of the wash basin, to measure a level of contamination of rinse fluid leaving the wash basin; and a processor and associated memory having instructions that when executed by the processor implement steps of receiving a signal from the contaminant sensor indicative of the level of contamination, and responsively determining the level of contamination and comparing the level of contamination with a contamination threshold to determine a hand washing status.

In some embodiments, the contaminant sensor may be one or more of a spectrometer, a refractive index sensor, a conductivity sensor, an inductive sensor, and a microscopic image or video sensor. Determining the hand washing status may include determining that the hand washing is complete.

The wash basin may be part of an integrated cleaning facility including an automated water facet. The system may also include a second sensor or sensors to determine the presence of a user's hands in a flow of rinse fluid into the wash basin. In some embodiments, the determination of the hand washing status is performed only when the user's hands are in the flow of the rinse fluid.

The system may also include a presence detector and a faucet, and the presence detector may be configured to turn on the faucet when a user or a user's hands are detected.

The system may also include an automated faucet, and the processor, upon determining that the hand cleaning status is that the cleaning is complete, may be configured to turn off the automated faucet.

The system may also include an audio or visual signal indicator. Determining the hand washing status may include issuing a notification of hand washing completion as a visual or audible alert on the signal indicator. The signal indicator may provide a first light indication while the user's hands are being cleaned and a second light indication to indicate the hand cleaning status when hand cleaning is complete.

The system may also include a display screen, and the processor may be configured to display on the display screen an instruction to continue washing until the hand washing is complete. The processor may also be configured to display on the display screen a notification of hand washing completion, when the hand washing status is that cleaning is complete.

The system may also include an identification (ID) reader and the processor may be configured to receive and store a user ID and the hand washing status. The ID reader may be configured to read one or more of a Radio Frequency Identification (RFID) tag, a Near Field Communication (NFC) tag, a magnetic card, a card with a smart chip, or a card with a visual barcode or QR symbol. The ID reader may be a biometric module including one or more of: a camera with a face recognition system, Time-of-Flight (ToF) cameras, a CMOS sensor, a voice recognition system, a touch or touchless fingerprint or hand sensor, or an iris identification sensor. In some embodiments, the system includes a communications link and a remote server, and the processor is further configured to transmit to the remote server the user ID together with the hand washing status.

The system may also include a communications link to a local or remote server. Determining the level of contamination may include transmitting the signal from the contaminant sensor over the communications link to the server, and processing the signal at the server to determine the hand washing status.

The system may also include a cleaning reagent dispensing unit controlled by the processor. The cleaning reagent of the cleaning reagent dispensing unit may include soap, foam, a chemical sanitizer, a biological sanitizer, or any combination thereof.

In some embodiments, parameters of the contamination threshold may be determined by a machine learning system, trained to correlate between one or more of the parameters and a level of hand cleanliness.

Also provided by embodiments of the present invention is a method for verifying hygienic hand cleaning including receiving a signal from a contaminant sensor positioned in proximity to a drain of a wash basin, so as to measure a level of contamination of rinse fluid leaving the wash basin; and responsively determining the level of contamination and comparing the level of contamination with a contamination threshold to determine a hand washing status.

BRIEF DESCRIPTION OF DRAWINGS

For a better understanding of various embodiments of the invention and to show how the same may be carried into effect, reference will now be made, by way of example, to the accompanying drawings. Structural details of the invention are shown to provide a fundamental understanding of the invention, the description, taken with the drawings, making apparent to those skilled in the art how the several forms of the invention may be embodied in practice. In the accompanying drawings.

DETAILED DESCRIPTION

Figure 1:
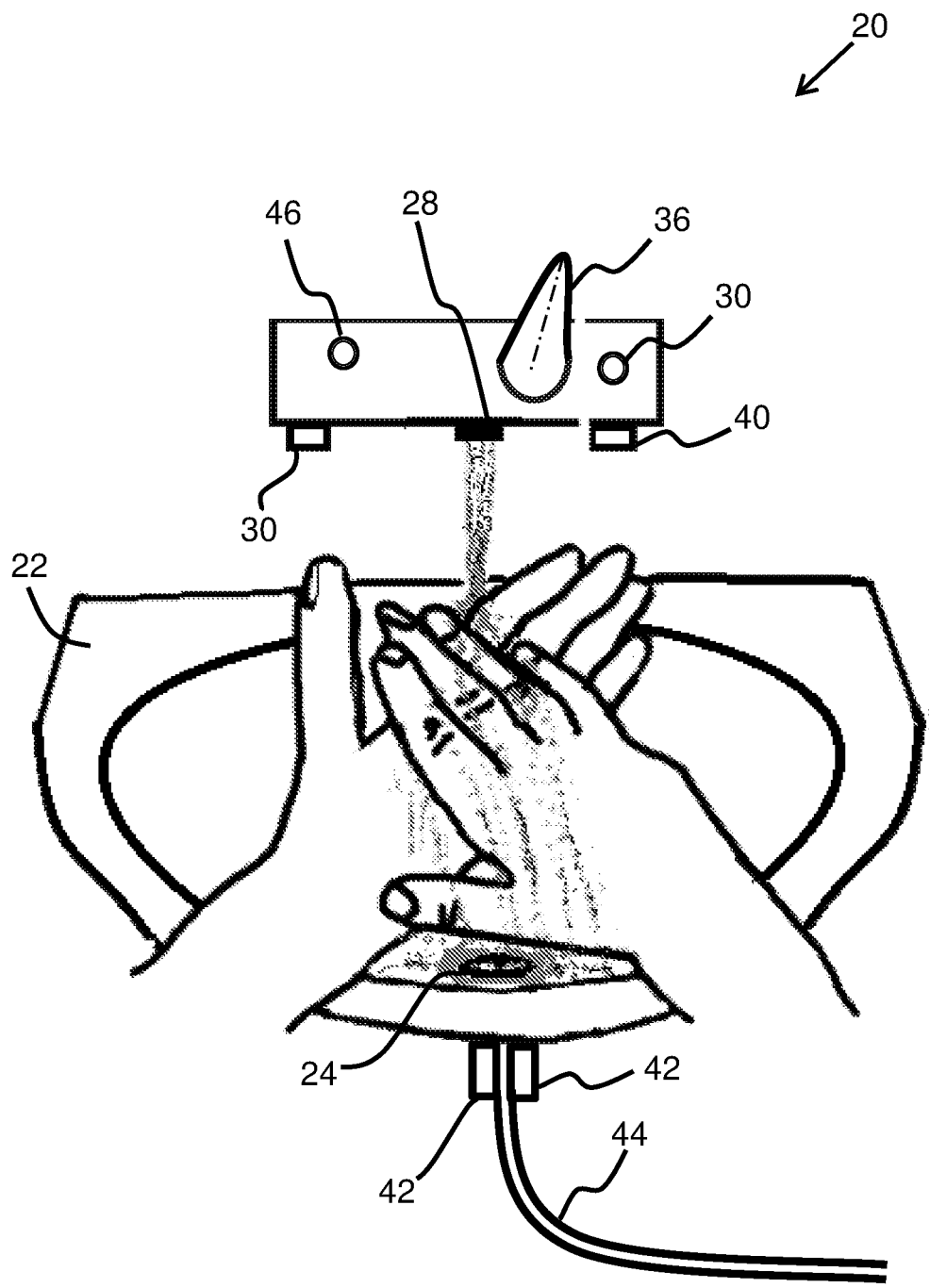
FIG. 1 is a schematic diagram of a system for verification of hygienic hand washing, according to some embodiments of the present invention.

It is to be understood that the invention and its application are not limited to the methods and systems described below or to the arrangement of the components set forth or illustrated in the drawings, but are applicable to other embodiments that may be practiced or carried out in various ways.

Embodiments of the present invention provide a system and methods for controlling and monitoring how an individual washes or sanitizes his or her hands, in order to verify that cleaning conforms with regulations and/or with medical recommendations for proper hygiene. The present invention typically includes a contaminant sensor to determine an extent of hand washing. When a level of contamination (or conversely, a level of purity) of the washing fluid (which may be water or other cleansing liquid, also referred to hereinbelow as the "rinse fluid") meets one or more predetermined criteria, such as levels of various contaminants being below (or above) preset thresholds, a determination is made that the hands are clean and that the hand washing is complete. Typically, the system provides a notification to a user to indicate that hand cleaning is complete, such as providing an audio or visual signal.

FIG. 1 is a schematic diagram of a system 20 providing verification of hygienic hand washing, according to some embodiments of the present invention. The system 20 may be an integrated cleaning facility as indicated hereinbelow with respect to FIG. 2, or it may be a cleaning facility in which the elements of the system are positioned in close proximity with each other but not necessarily in an integrated unit, as indicated in FIG. 1.

Typically, the system 20 includes a wash basin or sink 22, into which water or other rinse fluid flows into a drain 24. The rinse fluid may flow into the sink from a manual or automated faucet 28. Hereinbelow, water may be indicated as the rinse fluid, but it is understood that other rinsing fluids, such as water-based and or non-water-based antiseptic fluids, may also be employed.

Sensors of the system 20 may include one or more proximity or presence detectors 30 to detect the presence of a user and/or of a user's hands. The detection of the user and/or the user's hands may initiate the flow of rinse fluid by actuating the faucet 28. Subsequently, presence of the user's hands in the flow of water may be monitored as described further hereinbelow to confirm that the hands are being washed and that a purity level of the rinse water reflects the cleanliness of the hands.

Additionally or alternatively, system 20 may include a manual faucet handle 36 to control the water flow and the water temperature (e.g., the proportion of hot vs. cold water). In further embodiments, system 20 may include a thermal imager 40, such as one or more thermal imaging cameras or sensors, which may acquire thermal images or pixels of the hands while the hands are being washed and may also determine a water temperature. Alternatively or additionally, water temperature may be determined by a temperature gauge. The ambient air temperature may also be determined from the thermal images or from an additional temperature gauge. In some embodiments, the thermal imager 40 may also serve as the presence detector 30 of the system.

System 20 also includes one or more contaminant sensors 42, which may be positioned in proximity to the drain 24 of the wash basin 22, as indicated hereinbelow with respect to FIG. 2, or integrated into an outlet or drainpipe 44, as indicated in FIG. 1. Water temperature sensors may also be positioned by the drainpipe 44.

In embodiments of the present invention, the contaminant sensors 42 may include one or more of the following types of sensors:

1) Spectrometers, configured to measure spectral absorption, scattering, emissions, or other spectral phenomenon known in the art that provide spectral fingerprints of different elements or solvents in the rinse water. Spectral fingerprints may be detected for known molecules of organic and non-organic contaminants including microbiological contaminants, such as bacteria, viruses, protozoan, and parasites or any mixture of the above. A typical spectrometer sensor may be configured with a detection range of electromagnetic radiation having wavelengths between, for example, 200 to 1200 nanometers. Alternative or additional ranges that may detected may be in the near-infrared (NIR), mid-infrared (MIR), far-infrared (FIR), as well as ultraviolet (UV) ranges. Techniques of spectroscopy may employ Fourier-transform infrared spectroscopy (FTIR), RAMAN spectroscopy, fluorescence, and photoluminescence.

2) Refractive index sensors, which may measure the refractive index of the rinse fluid, which may change according to the type and concentration of contaminants.

3) Conductivity sensors, configured to measure the presence of ions of contaminants affecting the conductivity of the rinse fluid.

4) Magnetic sensors, configured to measure ferrous contaminants of the rinse fluid, such as iron, cobalt, nickel and their alloys, as well as compounds of some rare earth metals.

5) Microscopic image sensors, e.g., a digital microscope, with associated image processing configured to identify particles in recorded images, that is, contaminants, in the rinse fluid, including particle size and particle motion. The image sensor of the digital microscope may be, for example, a CCD (charge coupled device) or CMOS sensor.

Any of the above sensors, alone or in combination, may measure the rinse fluid (i.e., water or other solution) at the drain or outlet pipe to determine contamination levels, which may then been compared to thresholds for contaminants, typically preset, to determine when the contamination is sufficiently low (that is, the rinse fluid purity is sufficiently high) that the hand washing is complete (i.e., the hands are clean). The determination that hand washing is complete may also take into account additional factors, such as the rinse fluid temperature (which may be measured as described above) and the type of work environment.

Feedback to the user with respect to the level of contaminants measured during the washing process and/or the final determination that the hand washing is complete may be provided by a signal indicator 46. The signal indicator may be one or both of a speaker for issuing audio notifications or a light or display screen for issuing visible notifications, as described further hereinbelow.

Figure 2:
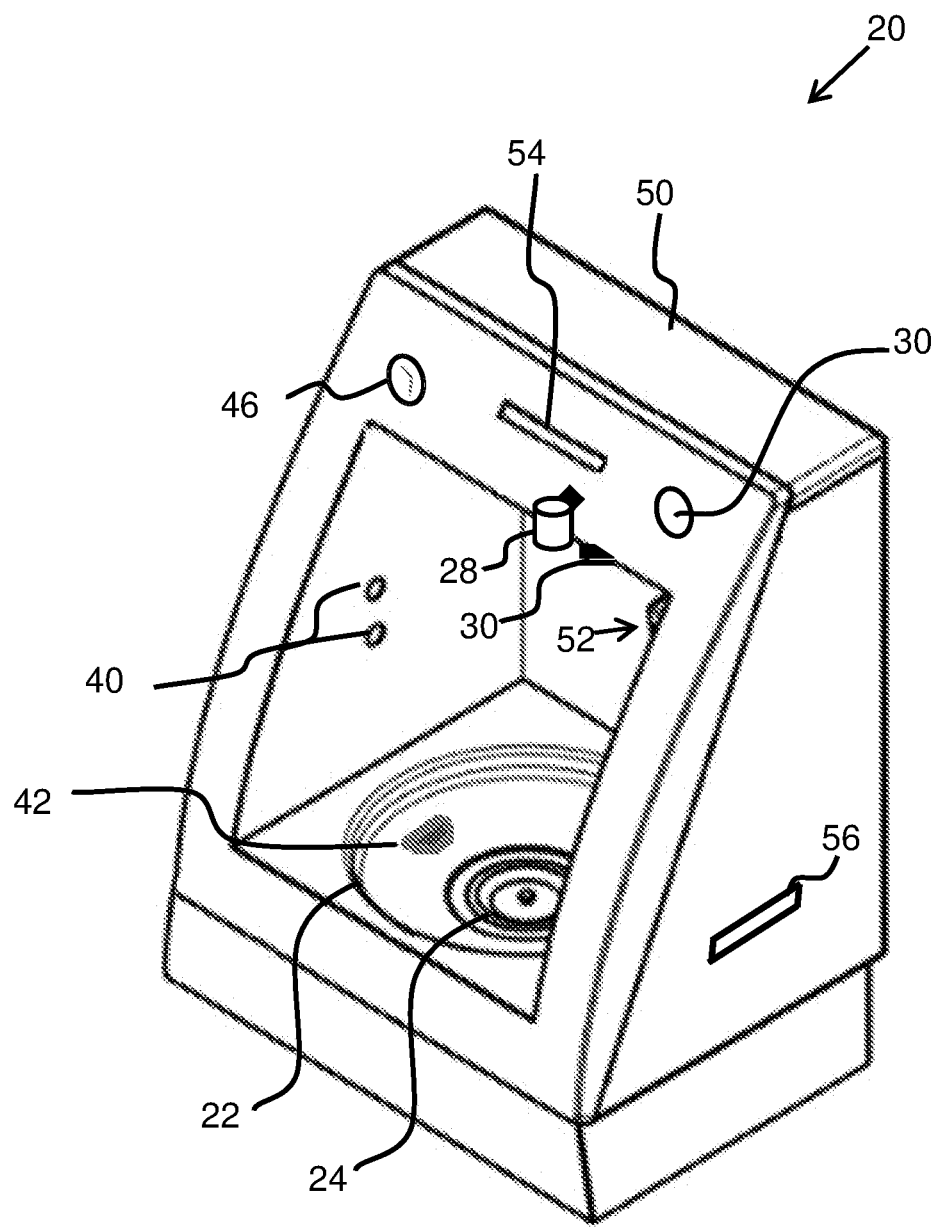
FIG. 2 is a schematic diagram of the system for verification of hygienic hand washing including an integrated facility, according to some embodiments of the present invention.

FIG. 2 is a schematic diagram of the system 20 for verification of hand washing including an integrated cleaning facility 50, according to some embodiments of the present invention. The integrated cleaning facility 50 may include in a single frame or unit the elements of system 20 indicated above with respect to FIG. 1. These elements typically include the wash basin 22, into which rinse fluid flows into the drain 24. The fluid (e.g., water or other solution) flows into the sink from the faucet 28. As indicated in the figure, sensors may include the presence detectors 30 and the thermal imager 40. The system also includes the contaminant sensor 42, which may be positioned in proximity to the drain 24 of the wash basin 22, as indicated in FIG. 2, or integrated into an outlet or drainpipe 44, as indicated in FIG. 1.

System 20 may also include a soap or sanitizing liquid dispenser 52. The dispenser may provide a soap or detergent, which may be any appropriate cleaning reagent, e.g., any soap, foam, chemical sanitizer, biological sanitizer, disinfecting solution of any type or any combination thereof. An additional element of system 20 may also be an identification (ID) reader 54 for identifying the ID of a user. When the user is identified, the processor may then record data regarding the user's hand cleaning completion, as well as additional data, such as the time and date and location, in order to maintain a record of employee hygiene and compliance with health regulations. The recorded data may, for example, be transmitted to a remote server that maintains such records.

The ID reader 54 may be, for example, a tag reader configured to read an identification (ID) of a personal tag of the user. The personal tag may be a Radio Frequency Identification (RFID) tag, a Near Field Communication (NFC) tag, a magnetic card, a card with a smart chip, or a card with a visual barcode or QR symbol. Alternatively or additionally, the ID reader 54 may be a biometric module configured to determine a user ID, such as a camera with a face recognition system, a computer vision module, a Time-of-Flight (ToF) camera, a CMOS sensor, a voice recognition system, a touch or touchless fingerprint or hand sensor, or an iris identification sensor.

Alternatively or additionally, the system 20 may also include a ticket or receipt dispenser 56, which, upon completion of the hand washing, may provide to the user a physical or electronic ticket or receipt as proof of proper completion (including, for example, a completion status with contamination statistics and a time of completion). Alternatively or additionally, the system 20 may include wireless communication means to transmit an authorization of hand washing completion and other hand washing status details to external devices, such as to a mobile device (e.g., smartphone or wearable device) of a user or to an external server as described below.

Figure 3:
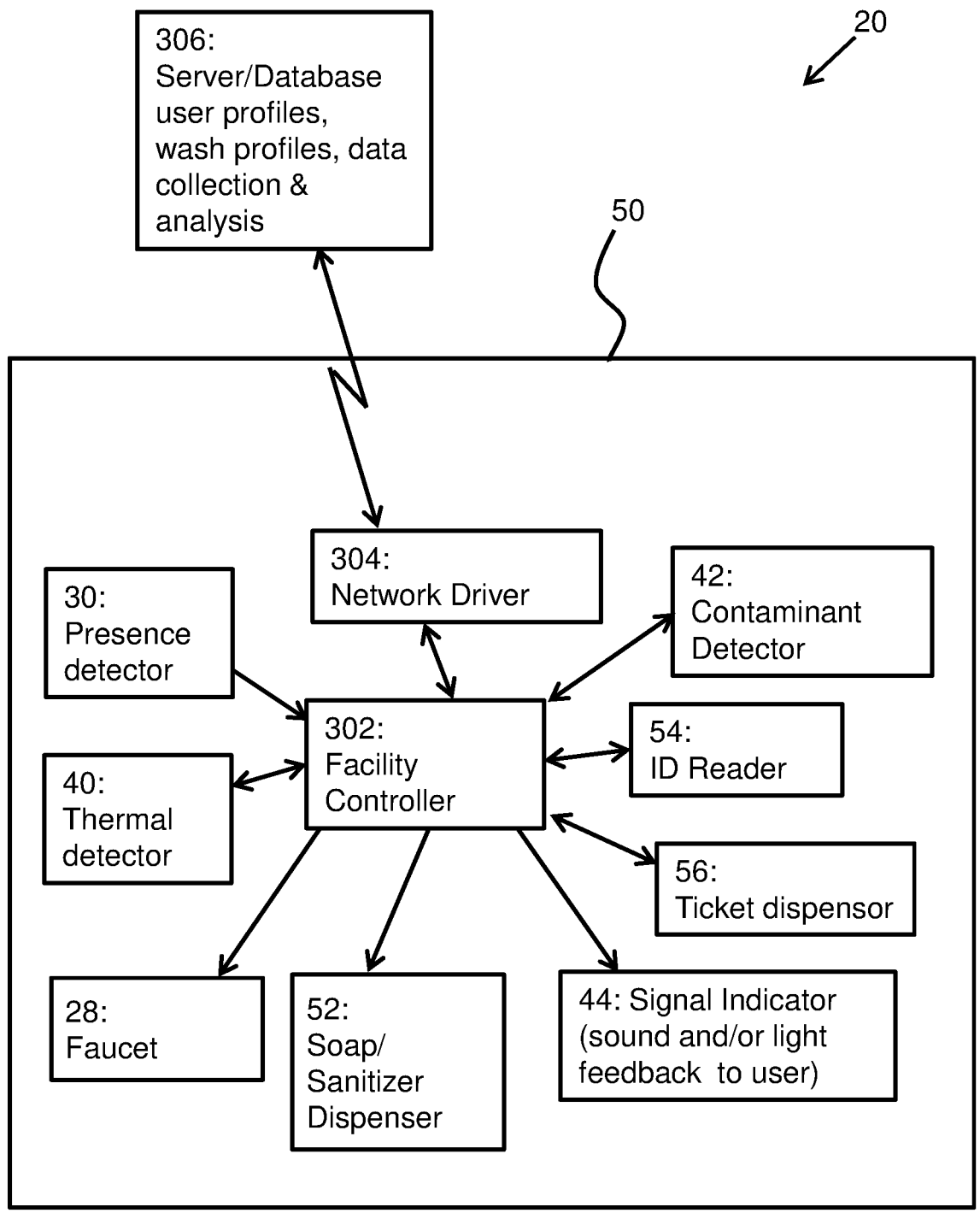
FIG. 3 is a block diagram of elements of the system for verifying hygienic hand washing, according to some embodiments of the present invention.

FIG. 3 is a block diagram of the system 20 for verification of hygienic hand washing, according to some embodiments of the present invention. System 20 may include, in addition to the components described above with respect to FIG. 1 and FIG. 2, a programmed processor or controller, indicated as a facility controller 302. The facility controller 302 is typically located in proximity to the wash basin, for example within the integrated cleaning facility 50, when the system is provided in an integrated configuration. The facility controller 302 provides signals to, and receives signals from, the other components of the system. For example, sensors such as the presence detector 30, the thermal imager 40, the contaminant sensor 42, and the ID reader 54 may send signals indicative of their respective measurements to the facility controller 50. The facility controller may process these signals to determine aspects of the status of the washing process, such as the presence of a user's hands in the flow of water, the water temperature, and the level of rinse water contamination.

The process of determining the level of rinse water contamination typically depends on the type or types of contaminant sensors employed. The sensors may be configured with internal processors to process the measurements acquired to determine contaminant levels or may transmit signals indicative of the measurements to the facility controller, which itself may be configured to process the measurements to determine contaminant levels. For example, a spectroscope may transmit spectrograms of light absorption measured from the rinse water. The spectrograms may be processed by the facility controller to determine, from the indicated absorption bands, the types and concentrations of contaminants present. Similarly, a digital microscopic imager may send images or raw visual signals to the facility controller, which may in turn be configured with image processing software to identify within the images particles that are indicative of contamination. Other sensors, such as refractive index, conductivity, and inductive sensors, may send signals indicative of an aggregated measure of contaminants, such that processing of the signals includes comparing the aggregated measures to preset thresholds to determine when washing is complete.

As mentioned above, spectroscopy techniques that may be employed may include FTIR, RAMAN, and ultraviolet-visible ("UV-Vis") spectroscopy. These methods typically measure how much light the rinse fluid absorbs at each wavelength. In "dispersive spectroscopy," a monochromatic light is generated, the amount of the light that is absorbed by the fluid is measured, and the process is repeated for multiple wavelengths in the measured range. In Fourier-transform spectroscopy, rather than shining a monochromatic beam of light into the fluid, a beam containing many frequencies of light is generated and the amount of light absorbed is measured. Then a new light beam containing a different combination of frequencies is generated and the absorption is measured. This process is repeated many times an algorithm is employed to calculate from the multiple absorption results the absorption at each wavelength.]

Also, as described above, spectroscopy may utilize one or more electromagnetic ranges, where the different ranges typically measure different physical properties of materials, which are correlated with various types of contamination. The near-IR range, with wavelengths of approximately 0.7-2.5 μm, excites modes of molecular vibrations. The mid-infrared wavelengths, of approximately 2.5-25 μm, indicate fundamental vibrations and associated rotational—vibrational structures of molecules. The far-infrared wavelengths, of approximately 25-1000 μm, may be used for rotational spectroscopy and low frequency vibrations. The terahertz band, of 1 mm to 0.1 mm, bordering the microwave region, excites intermolecular vibrations.

The facility controller 302 may also activate elements of the system according to the received signals from the different sensors of the system. For example, the facility controller may turn on the faucet 28 upon receiving a signal of a user's presence (or presence of a user's hands) from the presence detector 30. Similarly, the facility controller 302 may release soap from the dispenser 52, according to the presence of hands by the dispenser. Also according to the presence of a user and or user's hands, the facility controller 302 may trigger certain sensors, such as the ID reader 54 and the contaminant sensor 42, to begin operating.

From the signals of the contaminant sensor 42, the facility controller 302 determines levels of rinse water contaminants and responsively send signals indicative of these levels, or of an aggregated "percent purity," to the signal indicator 46, thereby providing cleaning status feedback to the user. The facility controller also compares the levels of rinse water contaminants with preset thresholds to determine when the hands are sufficiently clean and the washing is complete. Upon determining that the rinse water purity has reached a required threshold of purity, the facility controller may then send an appropriate signal to the signal indicator to generate a sound, such as a beeping sound or a spoken word or sentence. An example of such a sentence would be, for example, an audio announcement, "hands are clean." The facility controller may also turn on a light of the signal indicator, such as a green LED, to indicate completion of hand washing. Alternatively or additionally, the facility controller 50 may switch a light of the signal indicator from one color to another, such as switching a red light to a green light, indicating a change of a wash status from "washing in progress" to "washing complete." By way of further example, "washing in progress" may be indicated as a light set to a flashing state, which may then be changed to a constant light to indicate "washing complete."

Alternatively or additionally, the signal indicator 46 may be an LED screen, tablet, smartphone, touch screen or similar device on which the facility controller may display status words, or instructions, such as "Continue Washing," while hand cleaning proceeds, and "Washing Done" when the hand cleaning is determined to be complete. Other similar types of audio and/or visual user notifications to indicate wash status and completion may also be implemented. The facility controller 302 may also send similar indications to the signal indicator 46 to indicate whether or not the user's hands are sensed in the flow of the rinse fluid, according to signals provided by the presence detector or thermal imager. Typically, the facility controller is configured to determine that the washing is done only when the levels of contaminants are below preset thresholds while the user's hands are sensed as being in the flow of rinse fluid. (That is, the facility controller may be configured to ignore the contamination sensor signals when the hands are not positioned within the flow of rinse fluid, as in such a case the rinse fluid does not contain contaminants rinsed from the hands.)

In conjunction or in lieu of issuing a user notification that the washing is complete, the processor may also turn off the water faucet 28.

The facility controller 302 may also include a communications link, such as a network controller or driver 304, to communicate data to a remote server 306, which may be, for example, a cloud-based or data center-based server. As described above, the remote server may perform some of the processing of contaminant sensor data to determine contaminant levels.

The server described above may also store in a database the user ID and washing status, maintaining a log of when a user washed and the status of that cleaning (i.e., completed or not completed). Typically, a large organization may have multiple cleaning areas configured incorporating system 20 (e.g., bathrooms with multiple sinks, and multiple floors or buildings with respective bathrooms). The remote server 306 may include a centralized repository of cleaning records and user IDs. The remote server may also maintain "cleaning profiles," which may be transmitted to the facility controller to modify cleaning parameters, such as required level of purity with respect to different contaminants (e.g., a level of iron or of a certain type of virus or bacteria).

The cleaning profiles may include customized cleaning parameters for different users. For example, a cleaning profile for a user with sensitive skin may set parameters such that the cleaning process requires a shorter washing time. That is, parameters of the cleaning profiles may be a function of a particular user's allergies or sensitivities. Similarly, the parameters may be a function of regulatory requirements, which may change from time to time. Alternatively or additionally, the cleaning profiles may include customized cleaning parameters for different locations of a site (and for whether the cleaning is by washing or sanitizing). For example, a cleaning profile for a public bathroom of a facility may be set with different parameters than a sink accessible only to employees, particularly employees in requiring higher levels of sterility. Cleaning profiles may be determined by collecting data over the course of multiple hand cleanings and analyzing a correlation between one or more measurements of the contaminant sensors with levels of hand cleanliness that may be determined by measuring the surfaces of the hands. Hand surface measurements may be performed with methods known in the art, such as micobioligical swab tests or spectroscopy technologies for measuring hand surface contamination. Correlations may then be calculated by known mathematical methods as well as by training a machine learning system.

Figure 4:
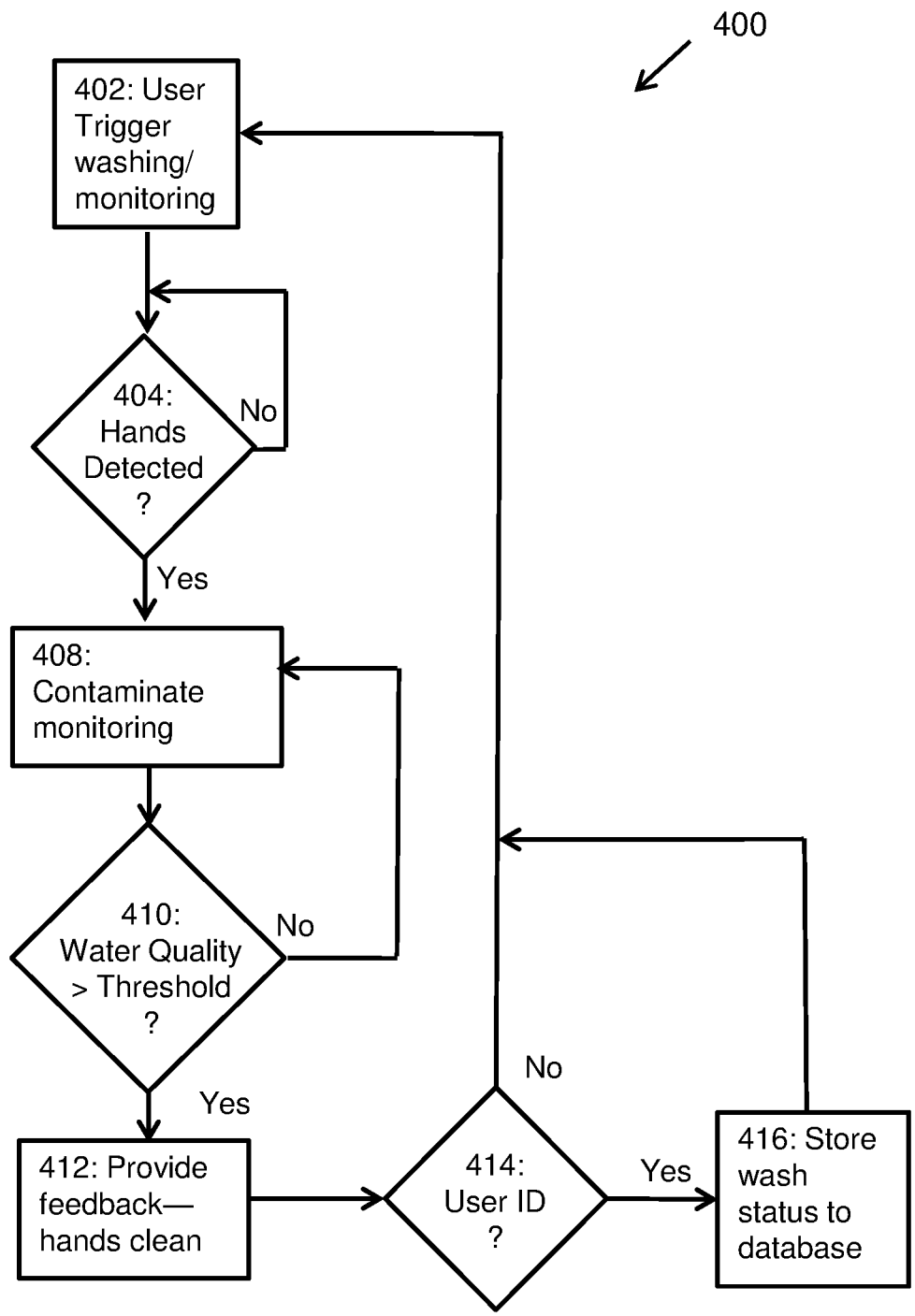
FIG. 4 is a flow diagram of a process for enhanced verification of hygienic hand washing, according to some embodiments of the present invention.

FIG. 4 is a flow diagram of a process 400 for verification of hygienic hand cleaning, according to some embodiments of the present invention. At an initial step 402, the cleaning process may be triggered by the facility controller 302 (indicated with respect to FIGS. 1-3) receiving a presence signal from the presence detector (detecting either a user or a user's hands), the thermal imager (detecting the user's hands), or by activation of the ID reader. Once the cleaning process is activated, the facility controller may load parameters of a cleaning profile, which may be stored locally (e.g., in memory of the facility controller) or received from a remote server, and which may be customized for a given location or user. The facility controller may also actuate the faucet to begin the flow of water into the wash basin. In some embodiments, the facility controller may maintain the flow of water only when the presence of hands in the flow of water is detected by the presence detector or thermal imager.

At a step 404, the facility controller may detect a user's hands, either by receiving a signal from a dedicated presence detector or by processing images of a camera or the thermal imager focused on the region of the wash basin in which a user would place his or her hands. Detection of the user's hands may trigger, at a step 406, operation of the contaminant sensor and acquisition of sensor data from the contaminant sensor (or sensors).

At a step 408, the facility controller may begin processing the sensor data from the contaminant sensor. Typically, the facility controller may continue to acquire signals from the presence detector under the washing is determined to be complete. As contaminant levels are determined, they may be compared with preset thresholds, which are set to establish when washing is complete. Typically, the levels of all measured contaminants must be less than the respective thresholds. Preset threshold may be set at more than zero contaminants, depending on the sensitive of the contaminant sensors and the work environment. As described above, the facility controller typically continues to monitor that the user's hands are in the flow of water, while minimizing "false negative" contamination signals when the hands are not positioned properly.

Once a determination has been made that the hand cleaning is complete, a notification may be provided to the user at a step 412, as described above. Alternatively or additionally, upon determining that the hand cleaning is complete the facility controller may close a valve of the faucet 28 to stop the flow of water or of the alternative rinsing fluid or other solutions).

At a step 414, a test is made as to whether the user ID was determined before or during the hand cleaning. If the user ID was determined, then at a step 416 the user ID, together with the cleaning status (e.g., the washing is complete, or not complete, or a measure of a percent of the cleaning that is complete, and the types and concentrations of contaminants detected, etc.) may be stored in a log file, and may also be transmitted to a central database or repository of a remote server as described above. The log file or database may also record the time of the hand cleaning. The log record of hand cleaning may be used subsequently by an organization to track compliance, or, for example, to provide an alert to the worker and/or to administrators that the worker has or has not completed a necessary hand cleaning process.

Once the step 416 is complete, the system is ready to receive a new user for a subsequent hand washing. It is to be noted that the process of hand washing may also be performed on users who are not identified, i.e., anonymous users, who may simply receive a notification as to whether or not the process is complete without a user ID being recorded. Anonymous users may also receive a physical indication, such as a ticket or receipt, as described above. An electronic indication may also be provided wirelessly to users. Such an indication may be provided to a user's mobile or wearable device, by standard communications means, such as Bluetooth, Wi-Fi, or SMS. In further embodiments, a log of anonymous hand cleaning may also be recorded.

Computational aspects of process 400 and of system 20 may be implemented in digital electronic circuitry, or in computer hardware, embedded firmware, software, or in combinations thereof. All or part of the process may be implemented as a computer program product, tangibly embodied in an information carrier, such as a machine-readable storage device or in a propagated signal, for execution by, or to control the operation of, data processing apparatus, such as a programmable processor, computer, or deployed to be executed on multiple computers at one site, or distributed across multiple sites, including cloud configurations. Memory storage may also include multiple distributed memory units, including one or more types of storage media. A computing system configured to implement the system may have one or more processors and one or more network interface modules. Processors may be configured as a multi-processing or distributed processing system. Network interface modules may control the sending and receiving of data packets over networks.

It is to be understood that the scope of the present invention includes variations and modifications thereof which would occur to persons skilled in the art upon reading the foregoing description and which are not disclosed in the prior art.

The invention claimed is:

1. A hand washing system, comprising:
   a wash basin, having a contaminant sensor positioned in proximity to a drain of the wash basin, wherein the contaminant sensor measures a level of contamination of rinse fluid leaving the wash basin;
   a processor and associated memory having instructions that when executed by the processor implement:
      receiving a signal from the contaminant sensor indicative of the level of contamination; and
      responsively, determining the level of contamination and comparing the level of contamination with a contamination threshold to determine a hand washing status.

2. The system of claim 1, wherein the contaminant sensor is one or more of a spectrometer, a refractive index sensor, a conductivity sensor, an inductive sensor, and a microscopic image sensor.

3. The system of claim 1, wherein determining the hand washing status comprises determining that the hand washing is complete.

4. The system of claim 1, wherein the wash basin is part of an integrated cleaning facility including an automated water facet.

5. The system of claim 1, further comprising a second sensor to determine the presence of a user's hands in a flow of rinse fluid into the wash basin, and wherein determining the hand washing status is performed only when the user's hands are in the flow of the rinse fluid.

6. The system of claim 1, further comprising a presence detector and a faucet, wherein the presence detector is configured to turn on the faucet when a user or a user's hands are detected.

7. The system of claim 1, further comprising an automated faucet, and wherein the processor, upon determining that the hand cleaning status is that the cleaning is complete, closes the automated faucet.

8. The system of claim 1, further comprising an audio or visual signal indicator and wherein determining the hand washing status comprises issuing a notification of hand washing completion as a visual or audible alert on the signal indicator.

9. The system of claim 1, further comprising a visual signal indicator, wherein the signal indicator provides a first light indication while the user's hands are being cleaned and a second light indication to indicate the hand cleaning status when hand cleaning is complete.

10. The system of claim 1, further comprising a display screen, wherein the processor is configured to display on the display screen an instruction to continue washing until the hand washing is complete.

11. The system of claim 1, further comprising a display screen, wherein the processor is configured to display on the display screen a notification of hand washing completion, when the hand washing status is that cleaning is complete.

12. The system of claim 1, further comprising an identification (ID) reader and wherein the processor is configured to receive and store a user ID and the hand washing status.

13. The system of claim 12, wherein the ID reader is configured to read one or more of a Radio Frequency Identification (RFID) tag, a Near Field Communication (NFC) tag, a magnetic card, a card with a smart chip, or a card with a visual barcode or QR symbol.

14. The system of claim 12, wherein the ID reader is a biometric module comprising one or more of: a camera with a face recognition system, Time-of-Flight (ToF) cameras, a CMOS sensor, a voice recognition system, a touch or touchless fingerprint or hand sensor, or an iris identification sensor.

15. The system of claim 12, further comprising a communications link and a remote server, and wherein the processor is further configured to transmit to the remote server the user ID together with the hand washing status.

16. The system of claim 1, further comprising a communications link and a remote server, wherein determining the level of contamination comprises transmitting the signal from the contaminant sensor over the communications link to the remote server, and processing the signal at the remote server to determine the hand washing status.

17. The system of claim 1, further comprising a cleaning reagent dispensing unit controlled by the processor.

18. The system of claim 17, wherein a cleaning reagent of the cleaning reagent dispensing unit comprises soap, foam, a chemical sanitizer, a biological sanitizer, or any combination thereof.

19. The system of claim 1, wherein one or more parameters of the contamination threshold are determined by a machine learning system, trained to correlate between one or more of the parameters and a level of hand cleanliness.

20. A method for verifying hygienic hand cleaning comprising:
receiving a signal from a contaminant sensor positioned in proximity to a drain of a wash basin, so as to measure a level of contamination of rinse fluid leaving the wash basin; and
responsively, determining the level of contamination and comparing the level of contamination with a contamination threshold to determine a hand washing status.

* * * * *